United States Patent [19]
Warren et al.

[11] Patent Number: 5,587,176
[45] Date of Patent: Dec. 24, 1996

[54] METHODS OF USING HESPERETIN FOR SEBUM CONTROL AND TREATMENT OF ACNE

[75] Inventors: Raphael Warren, Amberly Village; Adebola T. Akadiri, Cincinnati, both of Ohio

[73] Assignee: The Procter & Gamble Company, Cincinnati, Ohio

[21] Appl. No.: 361,906

[22] Filed: Dec. 21, 1994

Related U.S. Application Data

[63] Continuation of Ser. No. 49,923, Apr. 20, 1993, abandoned.

[51] Int. Cl.$^6$ .................................................... A61K 9/70
[52] U.S. Cl. ........................... 424/443; 514/25; 514/27; 514/456
[58] Field of Search ............................... 424/450, 443; 514/25, 27

[56] References Cited

U.S. PATENT DOCUMENTS 5,110,801  5/1992  LeVeen et al. ............................ 514/34

FOREIGN PATENT DOCUMENTS

| | | | |
|---|---|---|---|
| 0348509 | 3/1990 | European Pat. Off. | A61K 31/12 |
| 6211 | 9/1968 | France . | |
| 2084-021 | 4/1987 | Japan | A61K 31/35 |
| 62-145016 | 6/1987 | Japan | A61K 31/35 |
| 1096-126 | 4/1989 | Japan | A61K 31/35 |
| 2-193919 | 7/1990 | Japan | A61K 31/35 |
| 3-48617 | 3/1991 | Japan . | |
| 3-5423 | 3/1991 | Japan | A61K 31/35 |
| 3-188019 | 8/1991 | Japan . | |

OTHER PUBLICATIONS

Alcaraz M. J., M. L. Ferrandiz, and A. Villar, "Flavonoid Inhibition of Soybean Lipoxygenase", *Pharmazie*, vol. 41, pp. 299–300 (1986).

Kimmich G. A. and J. Randles, "Phloretin-like Action of Bioflavonoids on Sugar Accumulation Capability of isolated Intestinal Cells", *Membrane Biochemistry*, vol. 1, Nos. 3 & 4, pp. 221–237 (1978).

Middleton E., Jr., G. Drzewiecki, and J. Tatum, "The Effects of Citrus Flavonoids on Human Basophil and Neutrophil Function", *Planta Medica*, vol. 53, pp. 325–328 (1987).

Nishino C., N. Enoki, S. Tawata, A. Mori, K. Kobayashi, and M. Fukushima, "Antibacterial Activity of Flavonoids Against *Staphylococcus Epidermis*, a Skin Bacterium", *Agric. Biol, Chem.*, vol. 51, pp. 139–143 (1987).

Randles J. and G. Kimmich, "Effects of Phloretin and Theophylline on 3–O–methylglucose Transport by Intestinal Epithelial Cells", *American Physiological Society*, pp. C64–C72 (1978).

Welton A., L. Tobias, C. Fiedler–Nagy, W. Anderson, W. Hope, K. Meyers, and J. Coffey, "Effect of Flavonoids on Arachiodonic Acid Metabolism", *Plant Flavonoids in Biology and Medicine: Biochemical Pharmacological, and Structure–Activity Relationships*, pp. 231–242 (1986).

Wilkinson D. I. and E. K. Orenberg, "Effects of Nordihydroguaiaretic Acid, Phloretin, and Phloridzin on the Activity of Adenylate Cyclase, Lipoxygenase and Hexose Transport and Growth of Cultured Keratinocytes", *Pharmacology and Therapeutics*, vol. 26, pp. 660–666 (1987).

*Primary Examiner*—Samuel Barts
*Attorney, Agent, or Firm*—Milton B. Graff, IV; David L. Suter; Loretta J. Henderson

[57] ABSTRACT

The subject invention relates to methods for sebum control and treatment of acne in mammalian skin and scalp comprising administration of hesperetin, having the structure:

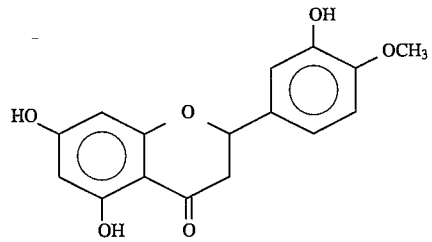

or a pharmaceutically-acceptable salt thereof.

16 Claims, No Drawings

METHODS OF USING HESPERETIN FOR SEBUM CONTROL AND TREATMENT OF ACNE

This is a continuation of U.S. patent application Ser. No. 08/049,923, filed on Apr. 20, 1993, now abandoned.

TECHNICAL FIELD

The present invention relates to the field of sebum control and treatment of acne in mammalian skin and scalp. Specifically, the invention relates to methods for sebum control and treatment of acne, and related pilosebaceous disorders, in human skin and scalp.

BACKGROUND OF THE INVENTION

The pilosebaceous gland is a principal source of oil on mammalian skin and scalp. Therefore, a benefit of controlling sebaceous gland activity (sebum secretion) includes a reduction in the level of oil found in skin and hair.

Sebum secretion is also related to acne. Acne is a pilosebaceous disease characterized by comedo, papules, inflamed nodules and superficial pus-filled cysts. The course and severity of acne is determined by the interaction between hormones, keratinization, sebum formation and bacteria. Acne usually begins at puberty, when the pilosebaceous glands increase in size and sebum synthetic activity is elevated due to increased circulating levels of androgens. Follicular hyperkeratosis can also occur, causing restriction of pilosebaceous follicles and, consequently, comedo or plug formation. The comedo contains sebum, protein debris, and anaerobic microorganisms including propionibacterium (corynebacterium) acnes (P. acnes). P. acnes thrive on the sebum and generates inflammatory free fatty acids (FFA). The FFA cause irritation in the follicular wall and can lead to rupture of the follicular wall, inducing an inflamed lesion. In severe cases, this lesion will heal with scarring.

Existing treatments for acne include from general topical application of lotions and salves to affected skin areas, to localized (spot) topical treatment. Products used for such treatments include benzoyl peroxide, sulfur resorcinol, salicylic acid and trans-retinoic acid. The therapeutic value is limited because of poor efficacy, poor aesthetics, and lack of effect on sebum production.

Other effective therapies for acne which reduce sebum production, include the use of antiandrogens, and cis-retinoic acid. However, because of undesirable systemic side effects, such as teratogenecity, pituitary dysfunction, and male sterility, current use is restricted to the more severe cases of acne. Antimicrobials are also somewhat effective in treating acne because they control the growth of P. acnes. The effectiveness of antimicrobials is limited because they do not affect sebum production.

It is an object of the subject invention to provide methods for the treatment of acne in mammalian skin.

It is also an object of the subject invention to provide methods for the treatment of acne in mammalian skin which reduce sebum and do not have the undesirable systemic side effects associated with antiandrogens, or retinoids.

It is a further object of this invention to provide methods for reducing oily skin and oily scalp or hair by controlling sebum production.

It is an even further object of the subject invention to provide methods for the treatment of acne in mammalian skin which control P. acnes growth.

SUMMARY OF THE INVENTION

The subject invention involves a method of treating acne in the skin of a mammal susceptible to or having acne, comprising application of a composition comprising a safe and effective amount of hesperetin, which has the structure:

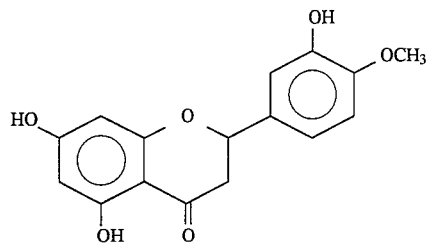

or a pharmaceutically-acceptable salt thereof. The subject invention also involves the treatment of oily conditions found in mammalian skin and scalp due to increased sebum production.

DETAILED DESCRIPTION OF THE INVENTION

It has been found in the subject invention that compositions containing hespererin reduce sebum production, preferentially partition into the sebaceous gland to promote sebum suppression activity, control P. acnes growth and activity, have anti-inflammatory activity, and lack the undesirable systemic side effects associated with antiandrogens. Furthermore, hespererin survives proteolytic activity in the gut and stomach and can therefore be effectively delivered in an oral dose form, in addition to being effective in a topical dose form. Thus, hespererin is a suitable active for both sebum control and for acne treatment.

As used herein, "topical application" means directly laying on or spreading on outer skin.

As used herein, "pharmaceutically-acceptable" means that salts, drugs, medicaments or inert ingredients which the term describes are suitable for use in contact with the tissues of humans and lower animals to which they will be exposed without undue toxicity, incompatibility, instability, irritation, allergic response, and the like, commensurate with a reasonable benefit/risk ratio.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors within the knowledge and expertise of the attending physician.

As used herein "treating sebaceous gland activity" means preventing, retarding and/or arresting the production of sebum.

As used herein "treating acne" means preventing, retarding and/or arresting the process of acne formation.

As used herein, "acne treatment agent" means an active capable of preventing, retarding and/or arresting the process of acne formation.

Active Agent

The subject invention involves a method for treating acne in mammalian skin by topically applying to the skin a safe and effective amount of hesperetin, which has the structure:

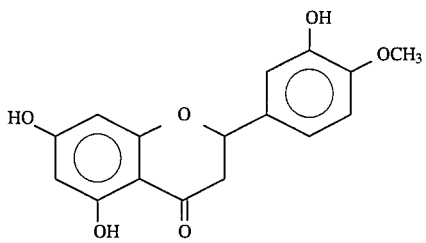

or a pharmaceutically-acceptable salt thereof. The subject invention also involves the use of hesperetin in controlling sebum production, thereby reducing the level of oil found in mammalian skin and scalp.

Preferred pharmaceutically-acceptable salts of hesperetin include alkali metal salts, such as sodium and potassium; alkaline earth metal salts, such as calcium and magnesium; non-toxic heavy metal salts; ammonium salts; and trialkylammonium salts, such as tdmethylammonium and triethylammonium.

The methods of the subject invention involve oral or topical application of a composition to mammalian skin and scalp, the composition comprising hesperetin as an active agent for treatment of acne or oily skin and scalp, and a pharmaceutically-acceptable carrier.

Pharmaceutically-Acceptable Carrier

In addition to the active agent as described hereinbefore, the pharmaceutical compositions of the present invention essentially comprise a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical compositions are capable of being comingled with the compound of the present invention, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as com starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; pyrogen-free water; isotonic saline; phosphate buffer solutions; cocoa butter (suppository base); emulsifiers, such as the Tweens®; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., NSAID drugs; pain killers; muscle relaxants) may be included in the pharmaceutically-acceptable carrier for use in the compositions of the present invention. For example, art-known local anesthetics may be included in the pharmaceutically-acceptable carrier (e.g., benzoyl alcohol; Novacaine®; lidocaine).

The choice of pharmaceutically-acceptable carrier to be used in conjunction with the compounds of the present invention is basically determined by the way the compound is to be administered. The preferred modes of administering the compounds of the present invention are orally and topically. Suitable pharmaceutically-acceptable carriers for topical application include those suited for use in creams, gels, solutions, lotions and the like. Carriers for oral administration include those suited for tablets and capsules.

The pharmaceutically-acceptable carrier employed in conjunction with the compounds of the present invention is used at a concentration sufficient to provide a practical size to dosage relationship. The pharmaceutically-acceptable carriers, in total, preferably comprise from about 60% to about 99.99999% by weight of the pharmaceutical compositions of the present invention, more preferably from about 80% to about 99.99%, more preferably from about 90% to about 99.95%, even more preferably still from about 95% to about 99.9%, also preferably from about 98% to about 99%. Representative compositions of the subject invention are provided in the Examples hereinafter.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art. Pharmaceutically-acceptable carriers useful in the compositions of the subject invention are described more fully hereinafter.

A. Oral Dose Forms

Various oral dosage forms can be used, including such solid forms as tablets, capsules, granules, bulk powders and microcapsules of the drug. These oral forms comprise a safe and effective amount, usually at least about 5%, and preferably from about 25% to about 50% of the compound of the subject invention. Tablets can be compressed, enteric-coated, sugar-coated or film-coated containing suitable binders, lubricants, surfactants, diluents, disintegrating agents, coloring agents, flavoring agents, preservatives, flow-inducing agents, and melting agents. Liquid oral dosage forms include aqueous and nonaqueous solutions, emulsions, suspensions, solutions and/or suspension reconstituted from non-effervescent granules, containing suitable solvents, preservatives, emulsifying agents, suspending agents, diluents, sweeteners, melting agents, coloring agents, and flavoring agents. Preferred carriers for oral administration include gelatin and propylene glycol. Specific examples of pharmaceutically-acceptable carriers and excipients that may be used in formulating oral dosage forms containing compounds of the subject invention are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated herein by reference. Techniques and compositions for making tablets (compressed, formulas and molded), capsules (hard and soft gelatin) and pills are described in *Remington's Pharmaceutical Sciences* (Arthur Osol, editor), 1553–1593 (1980), incorporated herein by reference.

The preferred unit dosage form for oral administration is tablets, capsules and the like, comprising a safe and effective amount of a compound of the subject invention. Preferably oral dose forms comprise from about 10 mg to about 3500 mg of a compound of the subject invention per dosage unit, more preferably from about 25 mg to about 1000 mg, and most preferably from about 50 mg to about 600 mg.

Topical Dose Forms

The compositions of the subject invention can also be administered topically to a biological subject, i.e., by the direct laying on or spreading of the composition on the skin of the subject. The topical compositions useful in the subject invention involve compositions suitable for topical application to mammalian skin, the composition comprising a safe and effective amount of the active hesperetin agent or mixture of such actives as described hereinafter, and a pharmaceutically-acceptable topical carrier. The subject compositions contain from about 0.01% to about 20%, preferably from about 0.05% to about 15%, more preferably from about 0.2% to about 10%, also preferably from about 1% to about 5% of the active agent.

The topical compositions useful in the subject invention may be made into a wide variety of product types. These include, but are not limited to lotions, creams, gels, sticks, sprays, ointments, pastes, mousses and cosmetics. These product types may comprise several types of carrier systems including, but not limited to solutions, emulsions, gels, solids, and liposomes.

The topical compositions useful in the subject invention formulated as solutions typically include a pharmaceutically-acceptable aqueous or organic solvent. The terms "pharmaceutically-acceptable organic solvent" refer to a solvent which is capable of having hesperetin dispersed or dissolved therein, and of possessing acceptable safety properties (e.g., irritation and sensitization characteristics). Water is a preferred solvent. Examples of suitable organic solvents include: propylene glycol, polyethylene glycol (200–600), polypropylene glycol (425–2025), glycerol, 1,2,4-butanetriol, sorbitol esters, 1,2,6-hexanetriol, ethanol, isopropanol, butanetriol, sorbitol esters, 1,2,6-hexanetriol, ethanol, isopropanol, butanediol, and mixtures thereof. These solutions useful in the subject invention preferably contain hesperetin from about 0.01% to about 15%, more preferably from about 0.1% to about 10%, and proferably from about 80% to about 99.99%, more preferably from about 90% to about 99% of an acceptable aqueous or organic solvent.

If the topical compositions useful in the subject invention are formulated as an aerosol and applied to the skin as a spray-on, a propellant is added to a solution composition. Examples of propellants is added to a solution composition. Examples of propellants useful herein include, but are not limited to, the chlorinated, fluorinated an chloro-fluorinated lower molecular weight hydrocarbons. A more complete disclosure of propellants useful herein can be found in Sagafin, *Cosmetics Science and Technology*, 2nd Edition, Vol. 2, pp. 443–465 (1972).

Topical compositions useful in the subject invention may be formulated as a solution comprising an emollient. Such compositions preferably contain from about 0.05% to about 5% of hesperetin and from about 2% to about 50% of a topical pharmaceutically-acceptable emollient. Such compositions preferably comprise a lipid soluble salt of hesperetin, such as a calcium salt.

As used herein, "emollients" refer to materials used for the prevention or relief of dryness, as well as for the protection of the skin. A wide variety of suitable emollients are known and may be used herein. Sagafin, *Cosmetics, Science and Technology*, 2nd Edition, Vol. 1, pp. 32–43 (1972), incorporated herein by reference, contains numerous examples of suitable materials.

A lotion can be made from a solution carrier system. Lotions typically comprise from about 0.01% to about 20%, preferably from about 0.1% to about 10%, of hesperetin; from about 1% to about 20%, preferably from about 5% to about 10%, of an emollient; and from about 50% to about 90%, preferably from about 60% to about 80% water.

Another type of product that may be formulated from a solution carrier system is a cream. A cream typically comprises from about 0.01% to about 20%, preferably from about 0.1% to about 10%, of hesperetin; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Ointment carriers may also be water soluble. An ointment may comprise from about 0.05% to about 10% of hesperetin, from about 2% to about 10% of an emollient plus from about 0.1% to about 2% of a thickening agent. A more complete disclosure of thickening agents useful herein can be found in Sagarin, *Cosmetics, Science and Technology*, 2nd Edition, Vol. 1, pp. 72–73 (1972).

If the carrier is formulated as an emulsion, preferably from about 1% to about 10%, more preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al.,; U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference. Preferred emulsifiers are anionic or nonionic, although the other types may also be used.

Lotions and creams can be formulated as emulsions as well as solutions. Typically such lotions comprise from about 0.01% to about 20%, preferably from about 0.1% to about 10%, of hesperetin; from about 1% to about 20%, preferably from about 5% to about 10%, also preferably from about 0.5% to about 5%, of an emulsifier. Such creams would typically comprise from about 0.01% to about 20%, preferably from about 0.1% to about 10%, of hesperetin; from about 1% to about 20%, preferably from about 5% to about 10%, of an emollient; from about 20% to about 80%, preferably from about 30% to about 70%, of water; and from about 1% to about 10%, preferably from about 2% to about 5%, of an emulsifier.

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. No.

4,254,105, Fakuda et al., issued Mar. 3, 1981, incorporated herein by reference, are also useful in the subject invention. In general, such single or multiphase emulsions contain water, emollients and emulsifiers as essential ingredients.

Triple emulsion carrier systems comprising an oil-in-water-in-silicone fluid emulsion composition as disclosed in U.S. Pat. No. 4,960,764, Figueroa, issued Oct. 2, 1990, are also useful in the subject invention. This triple emulsion carrier system is preferably combined with from about 0.01% to about 20%, more preferably combined from about 0.1% to about 10%, of hesperetin to yield a topical composition useful in the subject invention.

Another emulsion carrier system useful in the topical compositions is a micro-emulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is preferably combined with from about 0.1% to about 10% of hesperetin.

Liposomal formulations are also useful compositions of the subject invention. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", *Journal of Pharmaceutics and Pharmacology*, Vol. 34 (1982), pp. 473–474, incorporated herein by reference, or a modification thereof. Epidermal lipids of suitable composition for forming liposomes may be substituted for the phospholipid. The liposome preparation is then incorporated into one of the above topical carrier systems (for example, a gel or an oil-in-water emulsion) in order to produce the liposomal formulation. The final formulation preferably contains from about 0.1% to about 20%, more preferably from about 0.1% to about 10%, of hesperetin. Other compositions and pharmaceutical uses of topically applied liposomes are described in Mezei, M., "Liposomes as a Skin Drug Delivery System", *Topics in Pharmaceutical Sciences* (D. D. Breimer and P. Speiser, eds.,), Elsevier Science Publishers B. V., New York, N.Y., 1985, pp. 345–358, incorporated herein by reference.

If the topical compositions useful in the subject invention are formulated as a gel or a cosmetic stick, such compositions can be formulated by the addition of a suitable amount of a thickening agent, as disclosed supra, to a cream or lotion formulation.

The topical compositions useful in the subject invention may contain, in addition to the aforementioned components, a wide variety of additional oil-soluble materials and/or water-soluble materials conventionally used in topical compositions, at their art-established levels.

Various water-soluble materials may also be present in the compositions useful in the subject invention. These include humectants, proteins and polypeptides, preservatives and an alkaline agent. In addition, the topical compositions useful herein can contain conventional cosmetic adjuvants, such as dyes, opacifiers (e.g., titanium dioxide), pigments and perfumes.

The topical compositions useful in the subject invention may also include a safe and effective amount of penetration enhancing agent. A preferred amount of penetration enhancing agent is from about 1% to about 5% of the composition.

Other conventional skin care product additives may also be included in the compositions useful in the subject invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions useful in the subject invention. For example, Vitamin A, and derivatives thereof, Vitamin $B_2$, biotin, pantothenic, Vitamin D, and mixtures thereof may be used.

Cleaning Compositions

Skin and scalp cleaning compositions useful in the subject invention comprise, in addition to hesperetin, a cosmetically-acceptable surfactant. The term "cosmetically-acceptable surfactant" refers to a surfactant which is not only an effective cleanser, but also can be used without undue toxicity, irritation, allergic response, and the like. Furthermore, the surfactant must be capable of being comingled with the hesperetin in a manner such that there is no interaction which would substantially reduce the efficacy of the composition for treating acne and controlling sebum production.

The cleaning compositions useful in the subject invention preferably contain from about 0.01% to about 20%, more preferably from about 0.1% to about 10%, of hesperetin and preferably from about 1% to about 90%, more preferably from about 5% to about 10%, of a cosmetically-acceptable surfactant.

The physical form of the cleansing compositions is not critical. The compositions can be, for example, formulated as toilet bars, liquids, shampoos, pastes, or mousses. Toilet bars are most preferred since this is the form of cleansing agent most commonly used to wash the skin. Rinse-off cleansing compositions, such as shampoos, require a delivery system adequate to deposit sufficient levels of hespererin on the skin and scalp. A preferred delivery system involves the use of insolude complexes. For a more complete disclosure, see U.S. Pat. No. 4, 835,148, Barford et al., issued May 30, 1989; incorporated herein by reference in its entirety.

The surfactant component of the compositions useful in the subject invention are selected from anionic, nonionic, zwitterionlc, amphoteric and ampholytic surfactants, as well as mixtures of these surfactants. Such surfactants are well-known to those skilled in the detergency art.

The cleaning compositions useful in the subject invention can optionally contain, at their art-established levels, materials which are conventionally used in cleansing compositions. Nonlimiting examples of possible surfactants include isoceteth-20, sodium methyl cocoyl taurate, sodium methyl oleoyl taurate, and sodium lauryl sulfate. See U.S. Pat. No. 4,800,197, to Kowcz et al., issued Jan. 24, 1989, which is incorporated herein by reference in its entirety. Examples of a broad variety of additional surfactants useful herein are described in McCutcheon's, *Detergents and Emulsifiers*, North American Edition (1986), published by Allured Publishing Corporation, which is incorporated herein by reference in its entirety.

Combination Actives

A. Anti-Inflammatory Agents

An anti-inflammatory agent may be included as an active along with the hesperetin active agent, for treatment of acne. A safe and effective amount of an anti-inflammatory agent may be added to the compositions useful in the subject invention, preferably from about 0.1% to about 10%, more preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, fiunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use is hydrocortisone.

A second class of anti-inflammatory agents which is useful in the compositions includes the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference may be had to standard texts, including *Anti-inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974).

Specific non-steroidal anti-inflammatory agents useful in the composition invention include, but are not limited to:

1) the oxicams, such as piroxicam, isoxicam, tenoxicam, sudoxicam, and CP-14,304;
2) the salicylates, such as aspirin, disalcid, benorylate, trilisate, safapryn, solprin, diflunisal, and fendosal;
3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac;
4) the fenamates, such as mefenamic, meclofenamic, fluofenamic, niflumic, and tolfenamic acids;
5) the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and
6) the pyrazoles, such as phenylbutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical application. Of the nonsteroidal anti-inflammatory agents, ibuprofen, naproxen, flufenamic acid, mefenamic acid, meclofenamic acid, piroxicam and felbinac are preferred; ibuprofen, naproxen, and flufenamic acid are most preferred.

Finally, so-called "natural" anti-inflammatory agents are useful in methods of the subject invention. For example, candelilla wax, alpha bisabolol, aloe vera, Manjistha (extracted from plants in the genus Rubia, particularly *Rubia Cordifolia*), and Guggal (extracted from plants in the genus Commiphora, particularly *Commiphora Mukul*), may be used.

B. Retinoids

In a preferred acne-treating composition useful in the subject invention, a retinoid, preferably retinoic acid, is included as an active along with the hespererin active agent. The inclusion of a retinoid increases the acne-treating benefits of the composition. A safe and effective amount of a retinoid may be added to the compositions useful in the subject invention, preferably from about 0.001% to about 0.5%, more preferably from about 0.01% to about 0.1% of the composition. As used herein, "retinoid" includes all natural and/or synthetic analogs of Vitamin A or retinol-like compounds which possess the biological activity of Vitamin A in the skin as well as the geometric isomers and stereoisomers of these compounds, such as all-trans retinoic acid and 13-cis-retinoic acid.

C. Antimicrobial Agents

In a preferred acne-treating composition useful in the subject invention, an antimicrobial agent is included as an active along with the hesperetin active agent. The inclusion of an antimicrobial agent increases the acne-treating benefits of the composition. As used herein, "antimicrobial agent" means a compound capable of destroying microbes, preventing the development of microbes or preventing the pathogenic action of microbes.

A safe and effective amount of an antimicrobial agent may be added to compositions useful in the subject invention, preferably from about 0.001% to about 5%, more preferably from about 0.01% to about 2%, more preferably still from about 0.05% to about 1% of the compositions. Preferred antimicrobial agents useful in the subject invention are benzoyl peroxide, erythromycin, tetracycline, clindamycin, azelaic acid, and sulfer resorcinol.

D. Antiandrogens

In a preferred acne-treating composition useful in the subject invention, an antiandrogen is included as an active along with the hesperetin active agent. As used herein, "antiandrogen" means a compound capable of correcting androgen-related disorders by interfering with the action of androgens at their target organs. The target organ for the subject invention is mammalian skin.

A safe and effective amount of an antiandrogen may be added to the compositions useful in the subject invention, preferably from about 0.001% to about 5%, more preferably from about 0.01% to about 1%.

Antiandrogens which are androgen receptor antagonists as well as antiandrogens which are 5-α reductase inhibitors are useful in the compositions of the subject invention. Examples of such antiandrogens are more fully disclosed in U.S. Pat. No. 4,888,336, Holt, Metcalf and Levy, issued Dec. 19, 1989; U.S. Pat. No. 5,110,939, Holt, Metcalf and Levy, issued May 5, 1992; U.S. Pat. No. 5,120,742, Rasmusson and Reynolds, issued Jun. 9, 1992 and U.S. Pat. No. 4,859,681, Rasmusson and Reynolds, issued Aug. 22, 1989; all incorporated herein by reference. See also Stewart, M., and P. Pochi, "Antiandrogens and the Skin", *International Society of Tropical Dermatology*, Vol. 17, No. 3, pp. 167–179 (1978); incorporated herein by reference.

Preferred antiandrogens useful for compositions of the subject invention are cyproterone acetate, finasteride, chlormadinone acetate, 17-$\alpha$ propylmesterolone, 17-$\alpha$ estradiol acetate, dienoestrol diacetate, estradiol benzoate, inocoterone acetate, spirono-lactone, and 11-$\alpha$ hydroxyprogestrone.

E. Comedolytic Agents

In a preferred composition useful in the subject invention, a comedolytic agent is included as an active along with the hesperetin active.

As used herein, the term "comedolytic agent" refers to any compound capable of rupturing a comedo.

A safe and effective amount of a comedolytic agent may be added to the compositions useful in the subject invention, preferably from about 0.05% to about 10%, more preferably from about 0.1% about 5%.

A preferred comedolytic agent useful in the subject invention is salicylic acid.

Delivery Methods for the Topical Compositions

The topical compositions useful for the methods of the instant invention can be delivered from a variety of delivery devices. The following are two nonlimiting examples.

Medicated Cleansing Pads

The compositions useful herein can be incorporated into a medicated cleansing pad. Preferably these pads comprise from about 50% to about 75% by weight of one or more layers of nonwoven fabric material and from about 20% to about 50% by weight of a liquid composition deliverable from the nonwoven fabric material preferably comprising from about 0.01% to about 10% hesperetin, more preferably from about 1% to about 7% hesperetin. These pads are described in detail in U.S. Pat. No. 4,891,228, to Thaman et al., issued Jan. 2, 1990; and U.S. Pat. No. 4,891,227, to Thaman et al., issued Jan. 2, 1990; both of which are incorporated by reference herein in their entirety.

Dispensing Devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Nonlimiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve. The fluid preferably contains from about 0.01% to about 10% hesperetin, more preferably from about 1% to about 5% hesperetin.

The valve can include a diaphragm formed from an elastically fluid impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference in their entirety. Examples of applicators useful herein are commercially available from Dab-O-Matic, Mount Vernon, N.Y.

Methods for Treating Acne and Controlling Sebum

The present invention relates to methods for treating acne and controlling sebum in mammalian skin and scalp. Such methods may comprise topically applying to the skin an effective amount of the compositions of the subject invention. The term "effective amount", as used herein, means an amount sufficient to provide an anti-acne or sebum-control benefit. The composition can be applied for several days, weeks, months, or years at appropriate intervals: from about four times a day to about once every three days, preferably from about three times a day to about once every other day, more preferably about twice to once a day until existant acne subsides; and preferably from about twice a day to about once every other day, more preferably about once a day to prevent or retard the onset of acne. The composition is preferably applied from about twice a day to about once every three days, more preferably about once every other day to control oily skin and scalp.

Typically, in each application, an effective coating of the skin or scalp is achieved by applying from about 0.001 mg to about 5 mg per $cm^2$ skin or scalp per application of the active hesperetin agent, preferably from about 0.01 mg to about 2 mg per $cm^2$ skin or scalp per application, also preferably from about 0.05 to about 1 mg per $cm^2$ skin or scalp per application.

Oral administration can also be used through dosing of a pharmaceutical composition comprising a safe and effective amount of hesperetin in a suitable oral pharmaceutical carrier. The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

The amount of hesperetin ingested depends upon the bio-availability of hesperetin from the oral pharmaceutical composition. Typically, however, the hesperetin is dosed in an amount of from about 0.1 mg/kg of body weight to about 500 mg/kg, and preferably from about 1 to about 100 mg/kg of body weight. The oral dosage form of hesperetin is administered from about four times a day to about once every three days. For treatment of acne, the hesperetin is preferably administered from about three times a day to about once every other day, more preferably about twice or once a day. For sebum-control, the hesperetin is preferably administered from about twice a day to once every other day, more preferably about once a day. Generally, the oral pharmaceutical composition should comprise from about 5% to about 90% of hesperetin.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

ORAL DOSAGE FORMS

EXAMPLE 1

A tablet is prepared by combining the following components to homogeneity utilizing conventional mixing techniques:

| Ingredients | % Weight |
| --- | --- |
| Ascorbic Acid | 50 |
| Crystalline 9-Maltose | 32.5 |
| Cornstarch | 10 |
| Hesperetin | 7.5 |

The resultant mixture is tabletted with a 20R punch of diameter 12 mm. The product is an easily swallowable vitamin composition containing ascorbic acid and hesperetin.

Two of the resulting tablets, each containing 75 mg of the active are administered to a 60 kg human in need of treatment for oily skin once every other day until the skin condition subsides.

EXAMPLE II

A capsule is prepared by combining the following components utilizing conventional mixing techniques:

| Ingredients | Weight (mg) |
| --- | --- |
| Hesperetin | 50 |
| Silica Powder | 30 |
| Insoluble Crosslinked Polyvinylpirrolidone | 30 |
| Maize Starch | 20 |
| Sodium Carboxymethylcellulose | 10 |
| Polyvinylpirrolidone 30000 PM | 7 |
| Magnesium Stearate | 3 |

Two of the resulting capsules, each containing 50 mg of the active, are administered to a 60 kg human in need of treatment for existing acne every day. As acne subsides, dosing is reduced to one capsule every day.

EXAMPLE III

A capsule is prepared by combining the following components utilizing conventional mixing techniques:

| Ingedients | Weight (mg) |
| --- | --- |
| Hesperetin | 150 |
| Silica Powder | 60 |
| Maize Starch | 20 |
| Sodium Carboxymethylcellulose | 10 |

-continued

| Ingredients | Weight (mg) |
| --- | --- |
| Lactose | 30 |
| Magnesium Stearate | 3 |

One capsule is administered to a patient in need of treatment for existing acne two times daily. As the acne subsides, dosing is reduced to once daily.

TOPICAL DOSAGE FORMS

EXAMPLE IV

Topical compositions are prepared by combining the following components utilizing conventional mixing techniques:

| Ingredient | Composition 1 (% Weight) | Composition 2 (% Weight) | Composition 3 (% Weight) |
| --- | --- | --- | --- |
| Hesperetin | 0.1 | 1.0 | 10.0 |
| Ethanol | 10.0 | 15.0 | 15.0 |
| Glycerol | 1.0 | 2.0 | 3.0 |
| Perfume | 0.2 | 0.2 | 0.2 |
| Water | q.s. | q.s. | q.s. |

Any of the above compositions is applied to the face, to treat oily skin, at a dose of 0.2 ml, four times a day. As the skin becomes less oily, application is reduced to twice daily.

EXAMPLE V

Lotions are prepared, containing the following compositions, using conventional mixing techniques:

| Ingredient | Composition 1 (% Weight) | Composition 2 (% Weight) | Composition 3 (% Weight) |
| --- | --- | --- | --- |
| Hydroxylethyl Cellulose | 0.4 | — | 0.4 |
| Absolute Ethanol | 15.0 | 15.0 | 15.0 |
| Propane-1,2-diol | — | — | 30.6 |
| Butane-1,3-diol | 33.4 | 33.4 | — |
| Paramethyl Benzoate | 0.2 | 0.2 | 0.2 |
| Hesperetin | 1.0 | 10.0 | 20.0 |
| Perfume | 0.5 | 0.5 | 0.5 |
| Water | q.s. | q.s. | q.s. |

Use of an amount of any of the above compositions to deposit about 0.06 mg/cm$^2$ of the hesperetin to the scalp is appropriate to treat excess oil in the scalp. Application occurs about once a day. As the scalp becomes less oily, application is reduced to about once every other day.

EXAMPLE VI

A water-in-oil emulsion is prepared, by combining the following ingredients, using conventional mixing techniques:

| Ingredients | % Weight |
| --- | --- |
| Oily Phase | |
| Sorbitan monooleate | 20.0 |
| Quaternium-18-Hectonite | 5.0 |
| Liquid Parrafin | 60.0 |

-continued

| Ingredients | % Weight |
|---|---|
| Hesperetin | 15.0 |
| Aqueous Phase | |
| Xanthan Gum | 1.0 |
| Preservative | 0.3 |
| Perfume | 0.2 |
| Sodium Chloride (1% w/w) | q.s. |

The emulsion is prepared by taking 10 parts of the oily phase and adding to it slowly with stirring 90 parts by volume of the aqueous phase. Use of an amount of the emulsion to deposit about 0.02 mg/cm$^2$ of hesperetin to the skin is appropriate to treat existing acne. Application of the emulsion about twice a day is appropriate.

EXAMPLE VII

An oil-in-water cream is prepared by mixing the following components:

| Ingredient | % Weight |
|---|---|
| Oily Phase | |
| Cetearyl Alcohol | 5.0 |
| Silicon Oil, 200 Fluid | 1.0 |
| Isopropyl Myristate | 2.0 |
| Sodium Stearoyl-2-Lactylate | 2.0 |
| Hesperetin | 8.0 |
| Aqueous Phase | |
| Propylene Glycol | 5.0 |
| Sodium Citrate | 0.2 |
| Perfume | 0.1 |
| Water | q.s. |

The cream is prepared by mixing the oily phase and heating to 65° C. The aqueous phase is combined and heated to 70° C. The aqueous phase is added to the oil phase with suitable agitation. Moderate agitation is applied while cooling. Topical application of the cream is suitable to treat acne or control sebum. Use of an amount of the composition to deposit about 0.04 mg/cm$^2$ of hesperetin to the skin is appropriate to treat oily skin. Application occurs about once a day. When the skin becomes less oily, application is reduced to once every other day.

EXAMPLE VIII

The following lotions are prepared by mixing the ingredients in each composition according to conventional mixing techniques:

| Ingredient | Composition 1 (% Weight) | Composition 2 (% Weight) | Composition 3 (% Weight) |
|---|---|---|---|
| Benzoyl Peroxide | 2.0 | 5.0 | 10.0 |
| Absolute Ethanol | 40.0 | 40.0 | 40.0 |
| Propylene Glycol | 25.0 | 25.0 | 25.0 |
| Hesperetin | 10.0 | 5.0 | 0.5 |
| Perfume | 0.2 | 0.2 | 0.2 |
| Water | q.s. | q.s. | q.s. |

Any of the above compositions is applied to the face at a dose of 0.2 ml, four times a day to treat existing acne. As the acne subsides, application is reduced to once a day.

EXAMPLE IX

The following lotions are prepared by mixing the ingredients in each composition according to conventional mixing techniques:

| Ingredient | Composition 1 (% Weight) | Composition 2 (% Weight) | Composition 3 (% Weight) |
|---|---|---|---|
| Salicylic Acid | 0.5 | 2.0 | 5.0 |
| Absolute Ethanol | 40.0 | 40.0 | 40.0 |
| Propylene Glycol | 25.0 | 25.0 | 25.0 |
| Hesperetin | 10.0 | 1.0 | 5.5 |
| Perfume | 0.2 | 0.2 | 0.2 |
| Water | q.s. | q.s. | q.s. |

Use of an amount of any of the above compositions to deposit about 0.06 mg/cm$^2$ of hesperetin to the skin is appropriate to treat existing acne. Application occurs once a day.

EXAMPLE X

The following lotions are prepared by mixing the ingredients in each composition according to conventional mixing techniques:

| Ingredient | Composition 1 (% Weight) | Composition 2 (% Weight) | Composition 3 (% Weight) |
|---|---|---|---|
| Erythromycin | 0.5 | 2.0 | 4.0 |
| Absolute Ethanol | 40.0 | 40.0 | 40.0 |
| Propylene Glycol | 25.0 | 5.0 | 25.0 |
| Hesperetin | 10.0 | 1.0 | 5.0 |
| Perfume | 0.2 | 0.2 | 0.2 |
| Water | q.s. | q.s. | q.s. |

Use of an amount of any of the above lotions to deposit about 0.02 mg/cm$^2$ of hesperetin to the scalp is appropriate to treat excess oil in the scalp. Application occurs once every two days.

EXAMPLE XI

The following lotions are prepared by mixing the ingredients in each composition according to conventional mixing techniques:

| Ingredient | Composition 1 (% Weight) | Composition 2 (% Weight) | Composition 3 (% Weight) |
|---|---|---|---|
| Cyproterone Acetate | 0.5 | 1.0 | 5.0 |
| Absolute Ethanol | 40.0 | 40.0 | 40.0 |
| Propylene Glycol | 30.0 | 30.0 | 30.0 |
| Hesperetin | 5.0 | 1.0 | 5.0 |
| Perfume | 0.2 | 0.2 | 0.2 |
| Water | q.s. | q.s. | q.s. |

Use of an amount of any of the above compositions to deposit about 0.06 mg/cm$^2$ of hesperetin to the skin is appropriate to treat existing acne. Application occurs three times a day.

EXAMPLE XII

The following lotions are prepared by mixing the ingredients in each composition according to conventional mixing techniques:

| Ingredient | Composition 1 (% Weight) | Composition 2 (% Weight) | Composition 3 (% Weight) |
| --- | --- | --- | --- |
| Azelaic Acid | 1.0 | 5.0 | 20.0 |
| Absolute Ethanol | 40.0 | 40.0 | 40.0 |
| Propylene Glycol | 25.0 | 25.0 | 25.0 |
| Hesperetin | 10.0 | 2.0 | 5.0 |
| Perfume | 0.2 | 0.2 | 0.2 |
| Water | q.s. | q.s. | q.s. |

Any of the above compositions is applied to the face at a dose of 0.2 ml, three times a day to treat oily skin. As the skin becomes less oily, application is reduced to once a day.

EXAMPLE XIII

The following shampoo is prepared by mixing the ingredients according to conventional mixing techniques:

| | % Weight |
| --- | --- |
| Triethanolamine lauryl sulfate | 17.0 |
| Coconut diethanolamide | 2.0 |
| Hydroxypropylmethyl cellulose[1] | 0.2 |
| Corn syrup (80% solids)[2] | 30.0 |
| Dimethylpolysiloxane | 1.0 |
| Cationic cellulose[3] | 0.5 |
| Ethyl alcohol (SDA 40) | 9.0 |
| Vinyl carboxy polymer[4] | 0.7 |
| Hesperetin | 5.0 |
| Perfume, color, preservative | 1.0 |
| Water | q.s. |
| Acid or base to pH 6.5 | |

[1]Methocel E4M (Dow Chemical)
[2]42 Dextrose equivalent (Staley 1300)
[3]Polymer JR 400
[4]Carbopol 941 (BF Goodrich)

The composition is applied to the scalp every other day to treat excess oil in the scalp. A dose of about 0.5 ml is applied and washed off.

EXAMPLE XIV

The following hair tonic is prepared by mixing the ingredients according to conventional mixing techniques.

| | % Weight |
| --- | --- |
| Hesperetin | 2.0 |
| Pyroglutamic acid methyl ester | 10.0 |
| Ethanol | 40.0 |
| Perfume | 0.3 |
| Water | q.s. |

The composition is applied to the scalp every three days at a dose of about 0.4 ml to treat excess oil in the scalp. The tonic is left on after application.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A method of treating acne in mammalian skin comprising administering to a mammal susceptible to or having acne a composition consisting of a safe and effective amount of hesperetin having the structure:

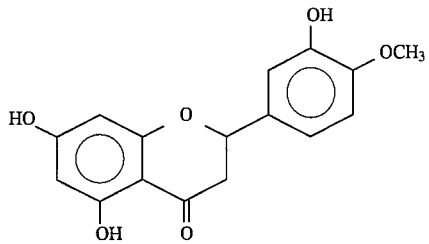

or a pharmaceutically-acceptable salt thereof.

2. The method of claim 1 wherein the composition is administered perorally.

3. The method of claim 2 wherein the hesperetin is administered in an amount of about 0.1 mg/kg of body weight to about 500 mg/kg of body weight of the mammal.

4. The method of claim 3 wherein the hesperetin is administered in an amount of about 1 mg/kg of body weight to about 100 mg/kg of body weight of the mammal.

5. The method of claim 1 wherein the composition is topically applied to the mammalian skin.

6. The method of claim 5 wherein the amount of hesperetin applied to the skin is from about 0.001 mg per $cm^2$ skin to about 5 mg per $cm^2$ skin.

7. The method of claim 6 wherein the amount of hesperetin applied to the skin is from about 0.01 mg per $cm^2$ skin to about 2 mg per $cm^2$ skin.

8. The method of claim 7 wherein the amount of hesperetin applied to the skin is from about 0.05 mg per $cm^2$ skin to about 1 mg per $cm^2$ skin.

9. The method of claim 5 wherein the composition is delivered from a pad comprising:

a) from about 50% to about 75% by weight of one or more layers of nonwoven fabric material; and b) from about 25% to about 50% by weight of a liquid composition, deliverable from the nonwoven fabric material, comprising from about 0.01% to about 10% by weight of hesperetin.

10. The method of claim 9 wherein the liquid composition comprises from about 1% to about 7% by weight of hesperetin.

11. A method of treating excessive sebaceous gland activity in mammalian skin and scalp comprising administering to a mammal susceptible to having excessive sebaceous gland activity a composition comprising a safe and effective amount of hesperetin having the structure:

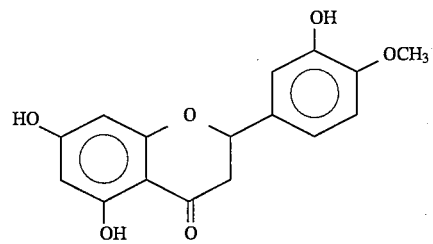

or a pharmaceutically-acceptable salt thereof.

12. The method of claim 11 wherein the composition is administered perorally in an amount of about 0.1 mg/kg of body weight to about 500 mg/kg of body weight of the mammal.

13. The method of claim 12 wherein the composition is administered perorally in an amount of about 1 mg/kg to about 100 mg/kg of body weight of the mammal.

14. The method of claim 11 wherein the composition is topically applied to the mammalian skin or scalp in an amount of about 0.001 mg per cm² skin to about 5 mg per cm² skin.

15. The method of claim 14 wherein the composition is topically applied to the mammalian skin or scalp in an amount of about 0.05 mg per cm² skin to about 1 mg per cm² skin.

16. A composition for the treatment of acne in mammalian skin for topical application to mammalian skin consisting of:
   a) a safe and effective amount of hesperetin having the structure:

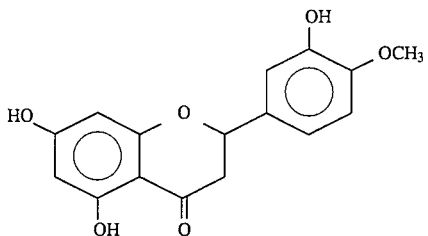

or a pharmaceutically-acceptable salt thereof; and
   b) a safe and effective amount of one or more compounds selected from the group consisting of cyproterone acetate, benzoyl peroxide, erythromycin, and azelaic acid.

* * * * *

UNITED STATES PATENT AND TRADEMARK OFFICE
CERTIFICATE OF CORRECTION

PATENT NO. : 5,587,176

DATED : Dec. 24, 1996

INVENTOR(S) : Warren et al.

It is certified that error appears in the above-identified patent and that said Letters Patent is hereby corrected as shown below:

In Col. 3, line 24, "Tdmethylammonium" should read --Trimethylammonium--.

In Col. 5, line 63, "Sagafin" should read --Sagarin--.

In Col. 6, line 8, "Sagafin" should read --Sagarin--.

In Col. 16, line 33, "5.0" should read --25.0--.

In Col. 17, line 33, "ªMethocel" should read --¹Methocel--.

Signed and Sealed this

First Day of June, 1999

Attest:

Q. TODD DICKINSON

Attesting Officer

Acting Commissioner of Patents and Trademarks